US006982164B2

United States Patent
Bassi et al.

(10) Patent No.: US 6,982,164 B2
(45) Date of Patent: Jan. 3, 2006

(54) UNHYDROLYZED JOJOBA PROTEIN PRODUCTS HAVING HIGH SIMMONDSIN CONCENTRATION

(75) Inventors: Sukh Bassi, Atchison, KS (US); Clodualdo C. Maningat, Platte City, MO (US); Dharmen Makwana, Platte City, MO (US); Ramaswamy Mani, Platte City, MO (US)

(73) Assignee: MGP Ingredients, Inc., Atchison, KS (US)

( * ) Notice: Subject to any disclaimer, the term of this patent is extended or adjusted under 35 U.S.C. 154(b) by 46 days.

(21) Appl. No.: 10/340,072

(22) Filed: Jan. 10, 2003

(65) Prior Publication Data

US 2004/0137091 A1    Jul. 15, 2004

(51) Int. Cl.
*A61K 6/00*    (2006.01)
*A61K 7/00*    (2006.01)
*C07K 1/00*    (2006.01)

(52) U.S. Cl. .................. 435/272; 435/262; 424/401

(58) Field of Classification Search ............... 435/262, 435/272; 424/401, 725, 400
See application file for complete search history.

(56) References Cited

U.S. PATENT DOCUMENTS 6,007,823 A * 12/1999 Abbott et al. ............... 424/776
6,552,171 B2 * 4/2003 Howard et al. ............. 530/377

OTHER PUBLICATIONS

1995 American Chemical Society, p. 1193–1197; New Simmondsin 2'–Ferulates from Jojoba Meal; M. Van Boven, P. Daenens and M. Cokelaere.

* cited by examiner

*Primary Examiner*—David M. Naff
*Assistant Examiner*—Deborah K. Ware
(74) *Attorney, Agent, or Firm*—Hovey Williams LLP

(57) ABSTRACT

Unhydrolyzed and hydrolyzed jojoba protein having high simmondsin concentration are provided. These jojoba proteins may be in the form of an aqueous dispersion containing a mixture of amino acids, peptides and/or protein fractions derived from the extraction and hydrolysis of naturally occurring jojoba protein, or dried into a powder.

3 Claims, 3 Drawing Sheets

Simmondsins Chromatogram From a Jojoba Meal Extract

US 6,982,164 B2

UNHYDROLYZED JOJOBA PROTEIN PRODUCTS HAVING HIGH SIMMONDSIN CONCENTRATION

BACKGROUND OF THE INVENTION

1. Field of the Invention

The present invention is broadly concerned with unhydrolyzed and hydrolyzed jojoba protein extracts having high concentrations of simmondsin and various other related glycosides and uses thereof, particularly in connection with cosmetic products such as shampoos, shampoo conditioners, hair styling gels, hair conditioners, hair reparatives, hair tonics, hair fixatives, hair mousses, bath and shower gels, liquid soaps, moisturizing sprays, makeup, pressed powder formulations, lip products, bath additives, sanitizing wipes, hand sanitizers, premoistened towelettes, skin lotions and creams, shaving creams, and sunscreens. More particularly, it is concerned with hydrolyzed and unhydrolyzed jojoba proteins which are preferably in the form of a mixture of amino acids, peptides and/or protein fractions derived from the extraction and, in the case of hydrolyzed protein, the hydrolysis of naturally occurring jojoba protein; such mixtures, when used in cosmetic products provide enhanced properties.

2. Description of the Prior Art

Jojoba is a dioecious wind-pollinated shrub, reaching a height of 1–5 meters and having a long life span (100–200 years). Jojoba is cultivated mainly in Arizona, Northern Mexico, Argentina and Israel. Genetic variability in morphology, anatomy and physiology within the species is very large and enable selection of clones for high yield and other agricultural attributes. Leaves are xerophytic with a thick cuticle, sunken stomata. They contain special tissue with a high concentration of phenol compounds. Flowers are apetalous: the female ones are usually solitary, one per two nodes although flowers every node or in clusters are not rare. The male flowers are clustered. Flower buds form in the axiles of leaves solely on the new vegetative growth occurring during the warm seasons under favorable temperatures and water regime. New flower buds are dormant and will open only after a cool season with enough cold units for the fulfillment of their chilling requirements. Anthesis occurs in the spring when the soil and air temperature rise to above 15° C. Severe water stress prevents opening of flowers. The jojoba fruit is a capsule containing one to three dark brown seeds that normally range in their dry weight between 0.5–1.1 g and contains 44–56% wax. Fruits ripen during the spring and early summer and seeds fall to the ground in late summer.

Indigenous Amerinds in the Sonora and Baja, Calif. used jojoba seed and oil for cooking, hair care, and for treatments of many medical problems such as poison ivy, sores, wounds, colds, cancer and kidney malfunction. The oil is extracted from jojoba seed by conventional screw pressing techniques, leaving a residual defatted dry material which is high in native jojoba protein (typically on the order of 25–35% by weight protein) and the glucoside simmondsin (typically in the range of 11–18% by weight).

Jojoba oil is a light yellow liquid at room temperature and is made up of straight-chain esters of mono-unsaturated long chain fatty acids and fatty alcohols and has an average total carbon chain length of 42 carbons. The product may be isomerized, hydrogenated, sulfurized, chlorinated or transesterified, and has a wide range of industrial uses, mainly in cosmetics in which it is incorporated in formulations for skin care preparations such as lotions, moisturizers, massage oils, creams, hair care products, lipsticks, makeups and nail products. Other potential uses include pharmaceuticals and as extenders for plastics, printers inks, gear-oil additives and lubricants.

SUMMARY OF THE INVENTION

The present invention is directed to new jojoba protein compositions which contain high levels of simmondsin, namely unhydrolyzed and hydrolyzed jojoba proteins and derivatives thereof, as well as uses of such protein and simmondsin products in cosmetic formulations. The preferred jojoba protein and derivatives thereof in accordance with the invention comprise a mixture of amino acids, peptides and/or protein fractions derived from the extraction and optional hydrolysis of naturally occurring jojoba protein. Protein hydrolysis is preferably carried out enzymatically, but if desired acid hydrolysis can also be employed.

In more detail, the unhydrolyzed jojoba protein is typically in the form of a mixture having an amino acid, peptide and/or protein fragment molecular weight range of about 200–880,000. Methods of producing unhydrolyzed jojoba protein generally comprise forming an aqueous dispersion of defatted jojoba meal. The aqueous dispersion is then heated to a temperature between about 60–90° C., more preferably between about 70°–80° C., and most preferably to about 75° C. Heating the dispersion aids in extracting the protein from the jojoba meal. Once the extraction has been performed, the dispersion is filtered thereby forming a liquid permeate which comprises the unhydrolyzed jojoba protein and simmondsin. The permeate may then be dried, preferably spray dried, into an unhydrolyzed jojoba protein powder containing simmondsin.

The unhydrolyzed jojoba protein permeate may optionally undergo a hydrolysis operation thereby producing hydrolyzed jojoba protein typically in the form of a mixture having an amino acid, peptide and/or protein fragment molecular weight range of from about 75–5,000 with an average molecular weight of from about 1,500–2,500. During hydrolyzation processing, it is often desirable to membrane filter the hydrolysis products in order to segregate the peptides and/or protein fragments to achieve different molecular weight profiles. In one such preferred method, a hydrolyzed jojoba protein product of relatively high molecular weight is provided, with a molecular weight range for the respective peptides and/or fragments therein of from about 1,000–5,000 and with an average molecular weight of from about 2,000–4,000. Similarly, a lower molecular weight fraction (sometimes referred to as a jojoba amino acid fraction) is produced wherein the respective amino acids and peptides exhibit a molecular weight range of from about 75–1,000, with an average molecular weight of from about 100–300.

Unhydrolyzed and hydrolyzed jojoba protein and derivatives thereof can be produced as a dry powder or in the form of an aqueous dispersion. The dry unhydrolyzed jojoba protein powder comprises from about 10–30% by weight protein or protein derivatives, more preferably from about 15–20% by weight, and the dry hydrolyzed jojoba protein powder comprises from about 18–35% by weight protein or protein derivatives, more preferably from about 25–30% by weight. The dry hydrolyzed jojoba amino acid powder comprises from about 3–15% by weight amino acid, preferably from about 5–10% by weight.

As used herein, "derivatives" of hydrolyzed jojoba protein refers to changes in the structure of the individual amino acids, peptides and/or protein fragments produced by amino acid addition, deletion, replacement, substitution and/or modifications; mutants produced by recombinant and/or DNA shuffling; quaternized species; and all other chemically synthesized/modified forms of the individual amino acids, peptides and/or protein fragments which retain at least in part some activity of the initial hydrolyzed amino acids, peptides and/or protein fragments. One particularly preferred class of unhydrolyzed and hydrolyzed jojoba protein derivatives is the lipid derivatives, especially those synthesized using C12–C22 fatty acids.

The term "hydrolyzed jojoba protein" is intended to embrace and cover not only the amino acids, peptides and/or protein fractions derived from the hydrolysis of naturally occurring jojoba protein but also all "derivatives" as herein defined. Furthermore, it is understood that the term "hydrolyzed jojoba protein" refers to a mixture of amino acids, peptides and/or protein fractions derived from the hydrolysis of naturally occurring jojoba protein, rather than a single specific protein molecule.

Defatted jojoba meal includes a number of related glycosides which act as natural appetite suppressants. The principal glycoside is simmondsin [2-(cyanomethylene)-3-hydroxy-4,4-dimethoxy-cyclohexyl beta-D glucoside] which may comprise up to about 7% by weight of defatted jojoba meal. The dry powder of unhydrolyzed jojoba protein extracts of the present invention comprise significant amounts of simmondsin, preferably from about 11–18% by weight, and more preferably from about 12–15% by weight. In aqueous dispersions of the unhydrolyzed and hydrolyzed jojoba protein products, the simmondsin is included in the solid phase of the dispersion. As noted above, it is also possible to segregate the hydrolyzed jojoba peptides and/or protein fragments into a protein product of relatively high molecular weight and a lower molecular weight amino acid fraction. The jojoba amino acid fraction preferably comprises from about 1–3% by weight simmondsin (on a dry basis), while the hydrolyzed jojoba protein product of relatively high molecular weight comprises from about 5–15% by weight simmondsin (on a dry basis).

Simmondsin and various related glycosides found in jojoba meal have the general formula:

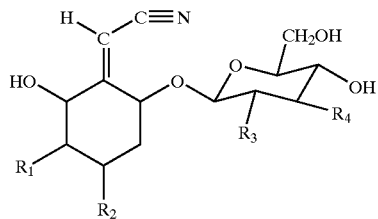

The specific formulas for simmondsin and several related glycosides are given in Table 1, wherein the trans-ferulic acid moiety (TFA) has the general formula:

TABLE 1

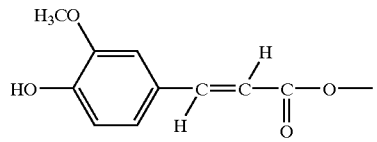

| Glucoside | $R_1$ | $R_2$ | $R_3$ | $R_4$ |
|---|---|---|---|---|
| Simmondsin | $OCH_3$ | $OCH_3$ | H | OH |
| 4-demethylsimmondsin | OH | $OCH_3$ | H | OH |
| didemethylsimmondsin | OH | OH | H | OH |
| simmondsin 2'-trans-ferulate | $OCH_3$ | $OCH_3$ | TFA | OH |
| simmondsin 4'-trans-ferulate | $OCH_3$ | $OCH_3$ | OH | TFA |
| 5-demethylsimmondsin 2'-trans-ferulate | $OCH_3$ | OH | TFA | OH |
| 4-demethylsimmondsin 2'-trans-ferulate | OH | $OCH_3$ | TFA | OH |

The ferulate simmondsin derivatives comprise about 9–16% by weight of the unhydrolyzed jojoba protein powder.

As used herein, the term "simmondsin" is intended to embrace not only the actual simmondsin glucoside molecule described above, but also generally, those related glycosides found in jojoba meal.

The jojoba products of the invention can be used to good effect in a variety of cosmetic formulations which include at least one ingredient selected from the group consisting of humectants, emollients, conditioners, thickeners, moisturizing agents, opacifiers, pearl agents, buffering agents, slip agents, feel agents, anti-static agents, acidifiers, preservatives, film formers, plasticizers, setting agents and suspending agents (usually, each of the foregoing ingredients when used is present at a level of from about 0.05–10% by weight). An amount of jojoba protein or derivative thereof is incorporated into this type of cosmetic formulation, usually at a level of from about 1–10% by weight, more preferably from about 3–8% by weight. As noted above, the jojoba protein (hydrolyzed or unhydrolyzed) will include an amount of simmondsin which has been carried through the extraction process. Preferably, the cosmetic formulations will comprise from about 0.05–2% by weight simmondsin, more preferably from about 0.5–1.5% by weight. Inasmuch as the preferred jojoba protein products are in the form of liquid dispersions, it is a simple matter to add the jojoba to the cosmetic formulations during preparation thereof. Generally, the formulation of the invention comprise from about 10–95% by weight water, more preferably from about 20–75% by weight water.

Among the cosmetic products which can benefit from incorporation of the jojoba products of the invention are those selected from the group consisting of shampoos, shampoo conditioners, hair styling gels, hair conditioners, hair reparatives, hair tonics, hair fixatives, hair mousses, bath and shower gels, liquid soaps, moisturizing sprays, makeup, pressed powder formulations, lip products, bath additives, sanitizing wipes, hand sanitizers, premoistened towelettes, skin lotions and creams, shaving creams, and sunscreens. In products of these types, the shampoos and shampoo conditioners further comprise at least about 6% by weight detergent; the hairstyling gels further comprise a gel-forming polymer system; the hair conditioners further comprise at least about 0.3% by weight cationic hair conditioner; the hair reparatives further comprise at least about 2% by weight cationic hair conditioner; the bath and shower gels further comprise at least about 25% by weight surfactant; the skin lotions and creams further comprise at least about 2% by weight of a cream former; the sunscreen further comprising a sunblocking agent; and the shaving creams further comprising at least about 10% by weight detergent and having a basic pH.

DETAILED DESCRIPTION OF THE PREFERRED EMBODIMENT

The following examples set forth preferred procedures for the production of unhydrolyzed and hydrolyzed jojoba protein and simmondsin, and use thereof in cosmetic products. It is to be understood, however, that these examples are provided by way of illustration and nothing therein should be taken as a limitation upon the overall scope of the invention.

EXAMPLE 1

This example describes a preferred procedure for the preparation of unhydrolyzed jojoba protein using defatted jojoba meal as a starting material. The meal is obtained from jojoba which has been conventionally press-treated to remove the jojoba oil, leaving the defatted meal. The meal has a protein content of 30.2% by weight, 38.3% by weight dietary fiber, 1.7% by weight residual oil, ash of 4.3% by weight, moisture of 5.6% by weight, with the remainder being insolubles. Defatted jojoba meal also comprises 11–18% by weight simmondsin and simmondsin related glycosides. The following table sets forth the amino acid profile of the protein fraction of the meal.

TABLE 2

| Ingredient | Amino Acid Profile |
| --- | --- |
| Aspartic Acid | 2.82% |
| Threonine | 1.41% |
| Serine | 1.53% |
| Glutamic Acid | 3.36% |
| Proline | 1.44% |
| Glycine | 2.45% |
| Alanine | 1.19% |
| Cystine | 0.80% |
| Valine | 1.54% |
| Methionine | 0.35% |
| Isoleucine | 1.03% |
| Leucine | 2.02% |
| Tyrosine | 1.07% |
| Phenylalanine | 1.23% |
| Histidine | 0.61% |
| Lysine | 1.45% |
| Arginine | 1.95% |
| Tryptophan | 0.32% |

Figure 3:
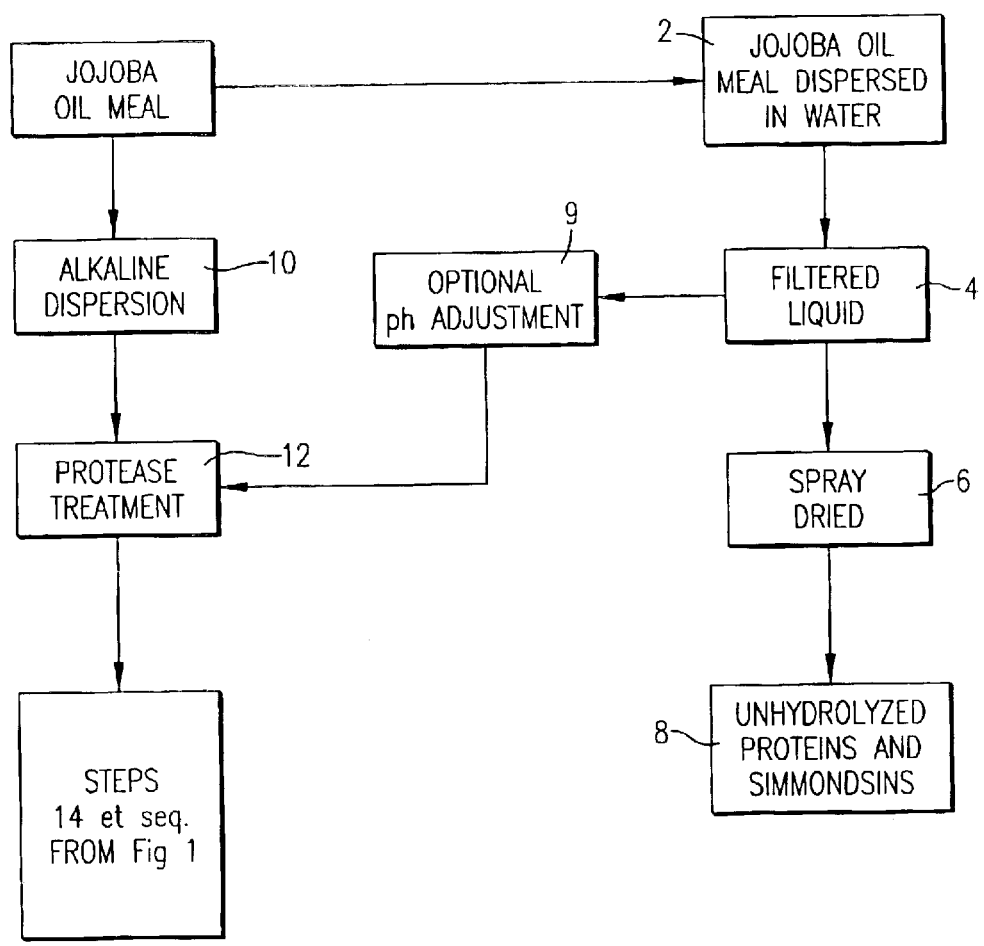
FIG. 3 is a schematic flow diagram illustrating the steps involved in the preferred process for the production of unhydrolyzed jojoba protein.

FIG. 3 schematically illustrates a preferred method of extracting unhydrolyzed jojoba protein. First, 1000 lbs. of defatted jojoba meal is mixed with 750 gallons of water for 45 minutes at room temperature (step 2). The resulting dispersion is heated to 165° F. (74° C.) and filtered (step 4). The permeate product is spray dried into a light tan colored powder (step 6). The resulting unhydrolyzed jojoba protein and simmondsin product 8 is analyzed. Product 8 has a moisture content of 4.5% by weight, a protein content of 15–20% by weight, and a total simmondsin content of 12–18% by weight. The molecular weight range for the protein is 200–880,000.

Figure 2:
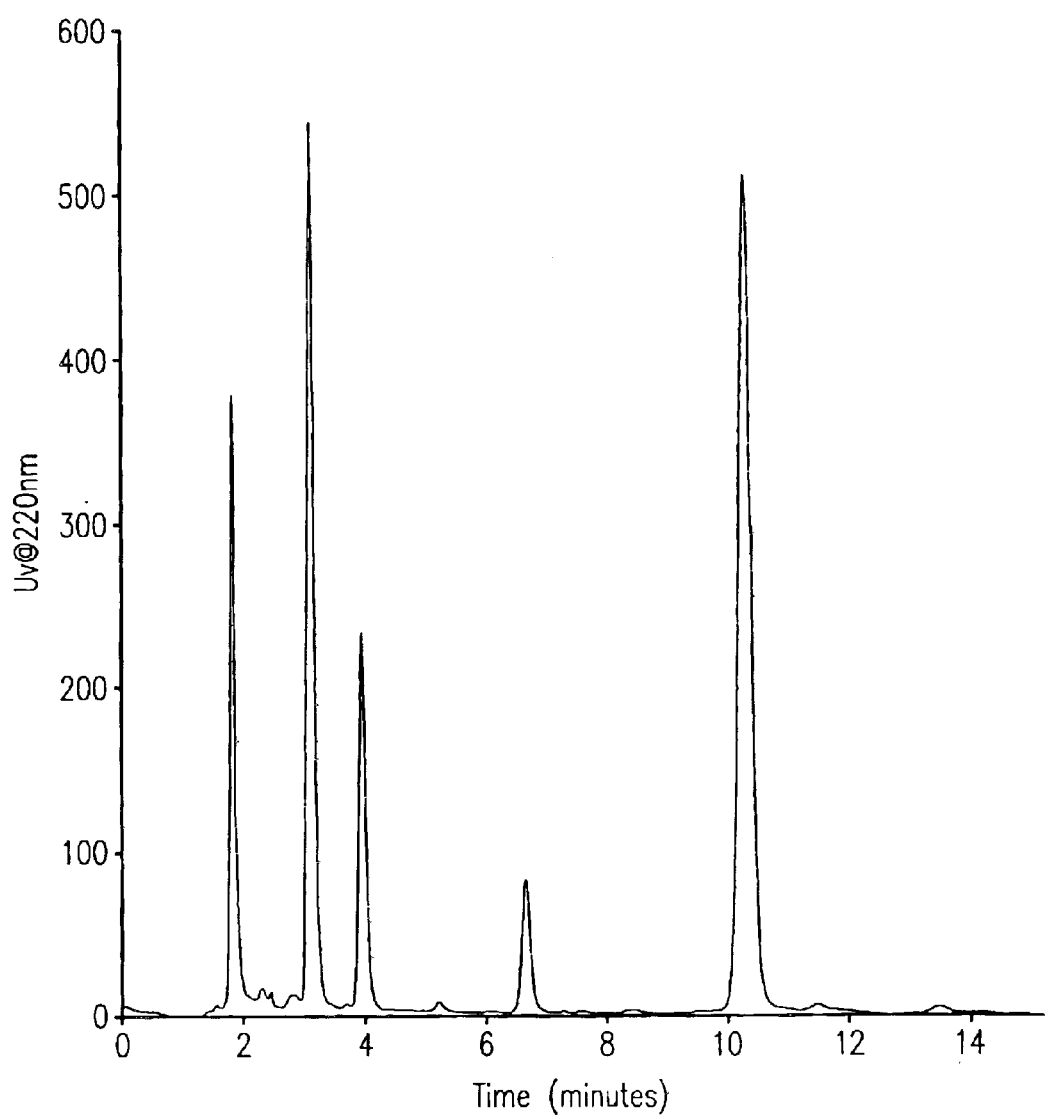
FIG. 2 is a typical HPLC simmondsin chromatogram from a jojoba meal extract.

FIG. 2 is an HPLC simmondsin chromatogram from the jojoba meal extract illustrating the various simmondsins which are present in the defatted jojoba meal.

The process described above may be altered in so that the unhydrolyzed jojoba protein contained within the permeate resulting from step 4 may be sent to an enzyme treatment process (step 12) where the jojoba proteins are hydrolyzed. Optionally, the pH of the permeate is adjusted prior to enzyme treatment (step 9). A preferred procedure for the preparation of hydrolyzed jojoba protein is described in Example 2 below.

EXAMPLE 2

This example describes a preferred procedure for the preparation of hydrolyzed jojoba protein, using defatted jojoba meal as a starting material. Defatted jojoba meal as described in Example 1 was used in this example.

Figure 1:
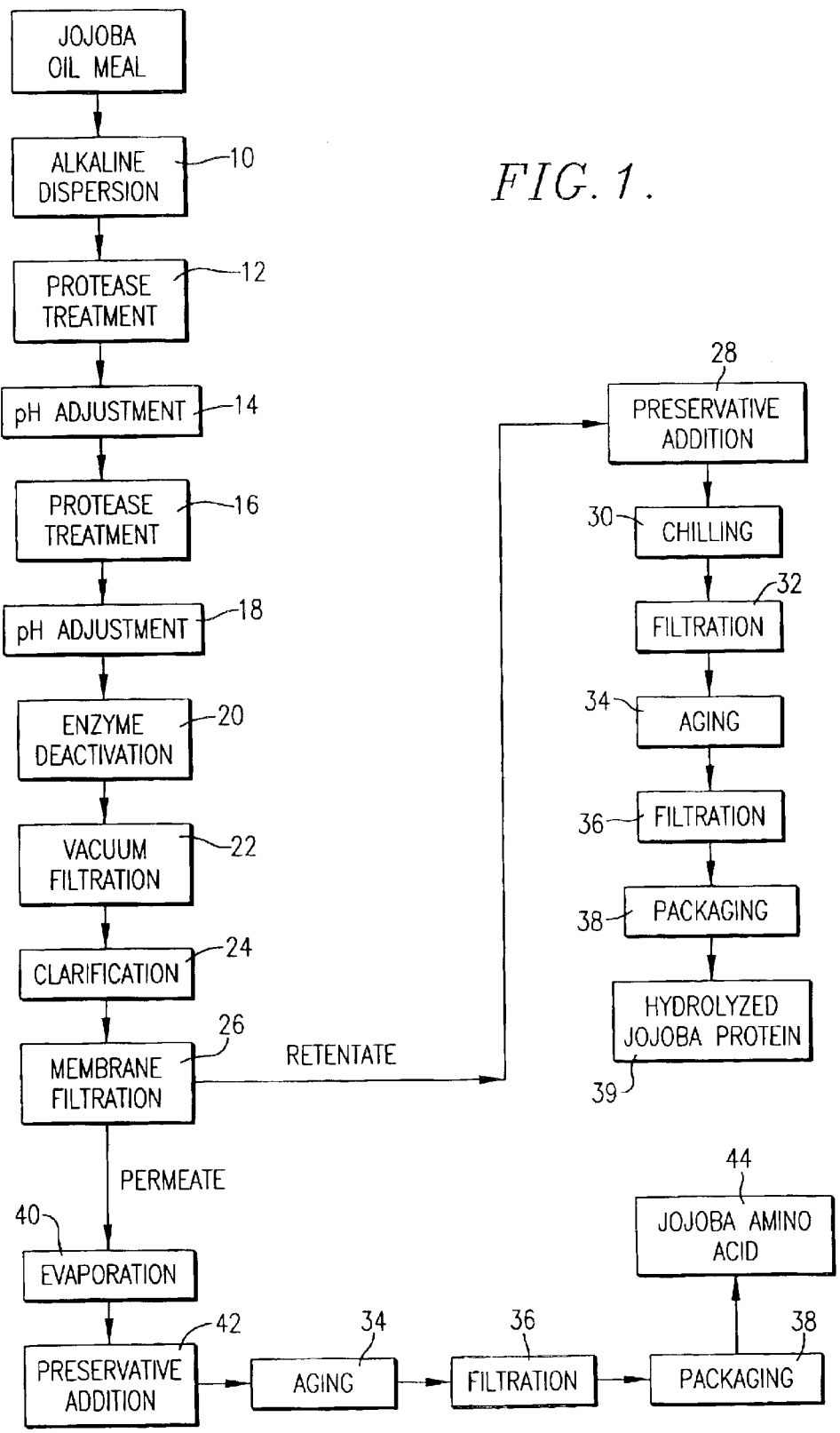
FIG. 1 is a schematic flow diagram illustrating the steps involved in the preferred process for the production of hydrolyzed jojoba protein.

The hydrolysis method is schematically illustrated in FIG. 1, and was carried out as follows. First, 750 gallons of soft water was heated to 140° F. and placed in a reaction tank. 1,000 pounds of the above-described jojoba oil meal was added to the reaction tank with agitation to completely disperse the meal. At this point, 22 pounds of 50% NaOH solution was added to the reaction tank for 1 hour to solubilize the proteins and create the alkaline dispersion 10 of FIG. 1.

In the next step, the protein slurry was treated with 15 pounds of protease enzyme (step 12), using a commercially available enzyme (Alcalase, Novo) and hydrolyzed for 2 hours with agitation. During this hydrolysis, the pH was maintained between 7.5–8.0 using 50% NaOH. A second dose of the Alcalase protease enzyme (15 pounds) was then added to the slurry followed by agitation for 2 hours. During this period, there was no pH adjustment.

In the next step 14, the pH of the slurry was adjusted to 6.5 using lactic acid, whereupon a second protease treatment (step 16) was carried out. This treatment included addition of 10 pounds of a second protease enzyme (Flavorzyme, Novo) followed by agitation for 4 hours. Thereupon, 3 pounds of Dual Protease Enzyme (Enzyme Development Corp.) was dispersed in 1 gallon of tap water and added to the slurry followed by the addition of 10 pounds of Neutrase (Novo). The slurry was then agitated for an additional 2 hours to continue the hydrolysis process.

In step 18, lactic acid was added to the slurry to lower the pH to 4.5, followed by the addition of 8 pounds sodium metabisulfite with agitation for 10 minutes. Next, in step 20, the slurry was heated to 160° F. to deactivate all protease enzymes.

The slurry containing hydrolyzed jojoba proteins was then processed in a rotary vacuum filter (step 22) to remove insolubles, and the filtrate was clarified by passage through a packed-house filter unit (step 24).

The clarified filtrate from step 24 was then fed to a nanofiltration membrane system, in order to generate a permeate and a retentate having different molecular weight profiles (step 26) after the retentate reached about 31% by weight solids using a refractometer. The membrane system was selected so that the lower molecular weight permeate proteins were generally below a molecular weight of 1,000, whereas the retentate proteins had a molecular weight of above about 1,000.

The retentate fraction was first treated by the addition of preservatives (step 28), namely 1% by weight Germaben II and 0.3% by weight Dowicil 200. The retentate was then chilled to 34–35° F. and allowed to stand for 16–24 hours (step 30). The chilled retentate was then cold-filtered in a packed-house filter unit to remove haziness (step 32), and additional preservatives were added (15% extra Germaben II and Dowicil 200).

The resulting retentate was aged 1–2 weeks (step 34) filtered (step 36) and packed in aqueous liquid form in 5-gallon jugs or 55-gallon drums (step 38) as hydrolyzed jojoba protein 39. This liquid contained about 10% by weight protein.

The permeate fraction was conventionally evaporated (step 40) to achieve a solids content of about 34% by weight, using a refractometer. Preservatives were then added (1% Germaben II and 0.3% Dowicil 200) followed by mixing for 1 hour (step 42). The retentate was then subjected to the same aging, filtration and packaging steps 34, 36 and 38 as the retentate, to produce aqueous liquid jojoba amino acid product 44. This liquid product contained about 4.5% by weight protein.

A molecular weight analysis of the hydrolyzed jojoba protein and amino acid products revealed that the higher molecular weight protein product was a mixture of peptides and/or protein fragments with a range of molecular weights of from about 1,000–5,000 and an average molecular weight of 3,500; the amino acid product was a mixture of amino acids and peptides with a range of molecular weights of from about 75–1,000, and average molecular weight of 200.

In particular, the jojoba amino acid product was analyzed to contain (wb) 0.28% aspartic acid, 0.13% threonine, 0.15% serine, 0.38% glutamic acid, 0.09% proline, 0.17% glycine, 0.17% alanine, 0.03% cysteine, 0.14% valine, 0.04% methionine, 0.09% isoleucine, 0.17% leucine, <0.01% tyrosine, 0.13% phenylalanine, 0.02% histidine, 0.08% lysine, 0.11% arginine, and <0.01% tryptophan.

It will be appreciated that the two products developed using this process comprise peptides and/or protein fragments derived from naturally occurring jojoba protein, and that the reference to "hydrolyzed jojoba protein" and "jojoba amino acid" is a convenience, merely referring to the fact that the respective mixtures have different molecular weight profiles. In both cases, however, the products are "hydrolyzed jojoba protein" and this term is used herein to refer to both of these products and for that matter any product containing amino acids, peptides and/or protein fragments derived from naturally occurring jojoba protein via hydrolysis.

EXAMPLE 3

In this example, a jojoba amino acid product is produced by acid hydrolysis of jojoba meal. In the process, 450 gallons of warm (160° F.) water is transferred to a homomixer tank, followed by the addition of 2 gallons of concentrated HCl (36%). The mixture is stirred and 950 pounds of jojoba meal is added, with continued stirring for 30 minutes. The acidified slurry is then transferred to a glass-lined reactor and 448 gallons of concentrated HCl (36%) is added to the reactor. The temperature of the mixture within the reactor is raised to 212–220° F. using a heat exchanger, followed by mixing for 24 hours. At the end of the 24 hour mixing period, the hydrolyzate is cooled to 120–140° F., and 50% NaOH solution is added to adjust the pH to 6.0–7.0. The neutralized hydrolyzate is then clarified using a rotary vacuum filter to remove solid particulates, and the clarified hydrolyzate is concentrated to the desired solids level (20–30%) in an evaporator.

Preservatives (1% Germaben and 0.3% Dowicil 200) are added. The product is then chilled at 34–35° F. for 16–24 hours. After chilling, the product is filtered using a packed-house filter unit to remove haziness. The product is then aged for 1–2 weeks, and a final filtration is carried out using a packed-house filter unit. The product is then packaged in suitable containers such as 5 gallon jugs or 55 gallon drums.

EXAMPLE 4

In this example, quaternized derivatives of hydrolyzed jojoba protein or jojoba amino acid are prepared. In the first step, 100 parts of the jojoba product (either hydrolyzed jojoba protein or hydrolyzed jojoba amino acid) are added to a reaction tank. The pH of the mixture is adjusted to 9.1–9.3 using 50% NaOH.

Seventeen parts by weight of 3-chloro-2-hydroxypropyl-N,N,N-dimethyldo-decylammonium chloride (Quab 342, 40% active) and 6 parts by weight of tap water are mixed in a separate container, followed by 1.7 parts by weight of 50% NaOH with agitation. The reaction is allowed to proceed for 10 minutes, giving a final pH typically between 10–11 (a small amount of additional 50% NaOH was added if the pH fell below 10). Alternatives to the Quab 342 product are 3-chloro-2-hydroxypropyl-N,N,N-dimethyloctadecylammonium chloride (Quab 426) or 3-chloro-2-hydroxypropyl-N,N,N-trimethylammonium chloride (Quat 188) to produce other derivatives. The solution in the separate container is then added to the pH-adjusted jojoba mixture, followed by agitation for 16–24 hours. The pH of the solution is then adjusted 4.4–4.6 using lactic acid (88%) solution. The product is then filtered using a packed-house filter unit to remove particulates, followed by packaging.

Chemically, the finished product is laurdimonium hydroxypropyl hydrolyzed jojoba protein (or laurdimonium hydroxypropyl jojoba amino acid). If Quab 426 is used, the product is steardimonium hydroxypropyl hydrolyzed jojoba protein (or steardimonium hydroxypropyl jojoba amino acid). If Quat 188 is used, the product is called hydroxypropyl trimonium hydrolyzed jojoba protein (or hydroxypropyl trimonium jojoba amino acid).

EXAMPLE 5

In this example, defatted jojoba meal comprising 6.10% by weight simmondsin (dry basis) is hydrolyzed into jojoba protein products 39 and 44 as described in Example 1. Products 39 and 44 undergo HPLC analysis to determine simmondsin content. Product 39 (hydrolyzed jojoba protein) is found to comprise 9.60% by weight simmondsin (dry basis) and product 44 (hydrolyzed jojoba amino acid) is found to comprise 1.53% simmondsin (dry basis).

It is important to note that the weight percentages expressed above are calculated on a dry basis. That is, products 39 and 44 are aqueous dispersions having a solid phase comprising hydrolyzed jojoba peptides and/or amino acid fragments. The weight percentage of simmondsin in the aqueous dispersion is determined by HPLC analysis. The weight percentage of simmondsin on a dry basis is back calculated taking into account the moisture content of the dispersion. The weight percentage on a dry basis represents the amount of simmondsin contained within the solids phase of the respective aqueous dispersion.

EXAMPLE 6

The following products were produced using the unhydrolyzed and hydrolyzed jojoba protein products described in Examples 1 and 2.

Ultra Shampoo

The following ingredients were used to prepare the shampoo.

TABLE 3

| Phase | Trade Name | INCI Name | Function | Amount |
|---|---|---|---|---|
| A | Distilled Water | Distilled Water | Aqua | Adjust |
| A | Merquat 550 | Polyquaternium-7 | Film Former | 0.05 |
| A | Stepanol WAC | Sodium Lauryl Sulfate | Cleansing | 10.00 |
| A | Stepanol CS-230 | Sodium Laureth Sulfate | Cleansing | 10.00 |
| A | Amphosol CA | Cocamidopropyl Betain | Foam Booster | 3.00 |
| B | Mackamide C | Cocamide DEA | Foam Booster | 1.00 |
| B | Jojoba Protein Powder | Unhydrolyzed Jojoba Protein | Reparative/Substantivity | 1.00 |
| B | Chamomile Extract | Chamomile Extract | Soothing | 0.07 |
| B | Calendula Extract | Calendula Extract | Healing | 0.05 |
| C | Preservative | QS | Antibacterial | QS |
| C | Fragrance | QS | Fragrance | QS |

Distilled water was placed in a primary tank and the remaining ingredients of Phase A were added, followed by those of Phases B and C, with mixing. pH was adjusted to 5.5–6.5 using 25% citric acid, and viscosity was adjusted with 10% NaCl solution.

Gentle Conditioning Agent

The following ingredients were used to prepare the conditioning agent.

TABLE 4

| Phase | Trade Name | INCI Name | Function | Amount |
|---|---|---|---|---|
| A | Distilled Water | Distilled Water | Aqua | QS |
| A | Aqua Pro II ™ QWt | Hydroxypropyltrimonium Hydrolyzed Wheat Protein | Conditioning | 2.00 |
| A | Lipowax G | Stearyl Alcohol | Emulsifier | 3.50 |
| A | Lipocol C | Cetyl Alcohol (Lipo) | Emulsifier | 3.00 |
| A | Lipocol C-20 | Ceatech-20 | Emulsifier | 2.50 |
| A | Beeswax White | Beeswax | Emulsifier | 0.25 |
| A | Dimethicone | Dow Corning 200 Fluid | Feel | 1.00 |
| A | Emulsifying Wax | Stearyl Alcohol/Ceteareth-20 | Emulsifier | 1.50 |
| B | Jojoba Protein Powder | Unhydrolyzed Jojoba Protein | Reparative | 1.00 |
| B | Chamomile Extract | Chamomile Extract | Soothing | 0.05 |
| B | Aloe Vera Extract | Aloe Vera Extract | Healing | 0.08 |
| B | Calendula Extract | Calendula Extract | Healing | 0.03 |
| B | Licorice Extract | Licorice Extract | Astringent | 0.08 |
| C | Preservative | QS | Antibacterial | QS |
| C | Fragrance | QS | Fragrance | QS |

Distilled water added to a primary tank followed by the ingredients of Phase A in the order listed, and the mixture was heated to 75° C. The mixture was then cooled to 35° C., and the Phase B and C ingredients were added. The pH was adjusted to 3.0 with 25% citric acid, and fragrance and preservative were added.

Moistirizing Body Wash

The following ingredients were used to prepare the body wash.

TABLE 5

| Phase | Trade Name | INCI Name | Function | Amount |
|---|---|---|---|---|
| A | Distilled Water | Distilled Water | Aqua | Adjust |
| A | Kessco EGMS 70 | Glycol Stearate | Emulsifier | 1.50 |
| A | Versene NA2 | Disodium EDTA | Chelation | 0.05 |
| A | Stepanol CS-230 | Sodium Laureth Sulfate | Cleaning | 20.00 |
| A | Amphosol CA | Cocamidopropyl Betaine | Foam Booster | 5.00 |
| B | Macamide C | Cocamide DEA | Foam Booster | 1.00 |
| B | Jojoba Protein Powder | Unhydrolyzed Jojoba Protein | Reparative/Moisturizer | 2.00 |
| B | Chamomile Extract (Active Organic) | Chamomile Extract | Soothing | 0.07 |
| B | Aloe Vera Extract (Active Organic) | Aloe Vera Extract | Healing | 0.05 |
| B | Calendula Extract | Calendula Extract | Healing | 0.05 |
| B | Glycerox HE | Peg-7Glyceryl Cocoate | Humectant | 0.50 |
| B | Aqua Pro II ™ WGO | Wheat Germ Oil | Anti-oxidant | .50 |
| C | Preservative | QS | Antibacterial | QS |
| C | Fragrance | QS | Fragrance | QS |

The product was prepared by placing an amount of distilled water in a primary tank and heating the water to 75° C., whereupon the remaining ingredients of Phase A were added with mixing. The mixture was then cooled to 45° C. and the ingredients of Phases B and C were added with adequate mixing. The pH of the mixture was then adjusted to 5.5–6.5 using 25% citric acid, and the viscosity was adjusted using a 10% NaCl solution.

Moisturizing Hand Cream

The following ingredients were used to prepare the hand cream.

TABLE 6

| Phase | Trade Name | INCI Name | Function | Amount |
|---|---|---|---|---|
| A | Distilled Water | Distilled Water | Aqua | QS |
| A | Carbopol 940 (2% solution) | Carbomer | Thickener | 0.15 |
| A | Propylene Glycol | Propylene Glycol | Humectant | 1.0 |
| A | Completech MBAC-DS | Milk Protein | Skin Feel | 0.50 |
| B | Stepan DGS SE | Triple Press Stearic Acid | Emulsifier | 3.00 |
| B | Lipocol C | Cetyl Alcohol | Emulsifier | 2.00 |
| B | Lipo GMS-450 | Glyceryl Stearate | Emulsifier | 1.75 |
| B | Shea Butter | Shea Butter | Emollient | 0.16 |
| B | Lipo IPP | Isopropyl Palmitate | Emollient | 1.00 |
| B | Lipo IPM | Isopropyl Myristate | Emollient | 1.00 |
| B | Crystisik NF 90 | Mineral Oil | Emollient | 0.50 |
| C | Skin-Flow C ™ | Wheat Starch Modified | Silky Feel | 2.00 |
| D | Japanese Green Tea Extract | Green Tea Extract | Astringent | 0.05 |
| D | Goldenrod Extract | Goldenrod Extract | Astringent | 0.05 |
| D | Aloe Vera | Aloe Vera | Healing | 0.05 |
| D | Yucca Extract | Yucca Extract | Stimulant | 0.03 |
| E | Jojoba Protein Powder | Unhydrolyzed Jojoba Protein | Anti-Wrinkle/Moisturizer | 1.00 |
| E | Jojoba Amino Acid | Jojoba Amino Acid | Moisturizer | 1.00 |
| E | Preservative | QS | Antibacterial | QS |

The distilled water and other ingredients of Phase A were placed in a primary tank and heated to 75° C. The ingredients of Phase B were placed in a secondary tank and also heated to 75° C. The Phase B ingredients were added to the Phase A ingredients at 75° C. with good agitation. The mixture was then allowed to cool and at 50–55° C. the ingredient of Phase C was added, making sure that there were no lumps or powder remaining in the tank. The ingredients of Phase D were then added in the order listed. The mixture was then allowed to cool to 35° C., whereupon the unhydrolyzed jojoba protein, jojoba amino acid product and preservative were added.

Anti-Wrinkle Cream

The following ingredients were used to prepare the anti-wrinkle cream.

TABLE 7

| Phase | Trade Name | INCI Name | Function | Amount |
|---|---|---|---|---|
| A | Distilled Water | Distilled Water | Aqua | QS |
| A | Carbopol 940 | Carbomer | Thickener | 0.20 |
| A | Glycerin | Glycerin | Humectant | 1.0 |
| A | Completech MBAC-DS | Milk Protein | Skin Feel | 0.50 |
| B | Stepan DGS SE | Triple Press Stearic Acid | Emulsifier | 3.00 |
| B | Lipocol C | Cetyl Alcohol | Emulsifier | 2.00 |
| B | Lipo GMS-450 | Glyceryl Stearate | Emulsifier | 1.75 |
| B | Promulgen D | Cetearyl Alcohol and Ceteareth-20 | Emulsifier | 1.00 |
| B | Coco Butter | Coco Butter | Emollient | 0.50 |
| B | Lipo IPP | Isopropyl Palmitate | Emollient | 1.50 |
| B | Lipo IPM | Isopropyl Myristate | Emollient | 1.50 |
| B | Crystosol NF 90 | Mineral Oil | Emollient | 0.50 |
| C | Skin-Flow-C ™ | Wheat Starch Modified | Silky Feel | 1.00 |
| D | Jojoba Protein Powder | Unhydrolyzed Jojoba Protein | Anti-Wrinkle | 2.00 |
| D | Jojoba Amino Acid | Jojoba Amino Acid | Anti-Wrinkle | 1.50 |
| E | Preservative | QS | Antibacterial | QS |

The distilled water was added to a primary tank followed by the ingredients of Phase A, with heating to 75° C. The Phase B ingredients were added in order to a secondary tank and heated to 75° C. Phase B was added to Phase A at 75° C. with good agitation with continued mixing and cooling to 50–55° C. At 50–55° C., the Skin-Flow-C product was added, making sure there were no lumps or powder remaining. When the temperature reached 35° C., the unhydrolyzed jojoba protein and jojoba amino acid were added, followed by the preservative.

Face Mask

The following ingredients were used to prepare the face mask.

TABLE 8

| Phase | Trade Name | INCI Name | Function | Amount |
|---|---|---|---|---|
| A | Aqua | Distilled Water | QS | QS |
| A | Versene NA | Disodium EDTA | Chelation | 0.10 |
| A | Propylene Glycol | Propylene Glycol | Humectant | 4.00 |

TABLE 8-continued

| Phase | Trade Name | INCI Name | Function | Amount |
|---|---|---|---|---|
| A | Stepanol CS-230 | Sodium Laureth Sulfate | Cleaning | 2.0 |
| A | Triethanolamine (99%) | Triethanolamine (99%) | pH Adjust | 1.00 |
| B | Sunflower Oil | Sunflower Oil | Emollient | 1.50 |
| B | Almond Oil | Almond Oil | Emollient | 0.50 |
| B | Jojoba Oil | Jojoba Oil | Emollient | 2.00 |
| B | Shea Butter | Shea Butter | Emollient | 1.00 |
| B | Lipocol S | Stearic Acid | Emulsifier | 4.50 |
| B | Lipocol GMS-450 | Glyceryl Stearate | Emulsifier | 2.50 |
| C | Carbopol 940 | Carbomer | Thickener | 0.80 |
| D | Yellow #6 | FD&C Yellow #6 | Colorifier | 0.01 |
| D | Bentonite 670 | Bentonite | Firming | 9.00 |
| D | Kaoline | Kaoline Colloidal NF | Firming | 7.00 |
| E | Jojoba Protein Powder | Unhdrolyzed Jojoba Protein | Anti-Wrinkle | 1.00 |
| E | Jojoba Amino Acid | Jojoba Amino Acid | Anti-Wrinkle | 1.00 |
| E | Preservative | QS | Antibacterial | QS |

Phase C was pre-mixed with 50% of the water from Phase A and when all of Phase C had dissolved, the solution was heated to 75° C., and the remaining Phases A, B and D were added. The mixture was cooled to 35° C., whereupon the Phase E ingredients were added.

Hair Shampoo

The following ingredients were used to prepare the shampoo.

TABLE 9

| Phase | Trade Name | INCI Name | Function | Amount |
|---|---|---|---|---|
| A | Distilled Water | Distilled Water | Aqua | Adjust |
| A | Versene NA2 | Disodium EDTA | Chelation | 0.05 |
| A | Stepanol CS-230 | Sodium Laureth Sulfate | Cleaning | 20.00 |
| A | Amphosol CA | Cocamidopropyl Betaine | Foam Booster | 3.00 |
| B | Macamide C | Cocamide DEA | Foam Booster | 1.00 |
| B | Jojoba Protein | Hydrolyzed Jojoba Protein | Reparative/ Moisturizer | 2.00 |
| B | Chamomile Extract (Active Organic) | Chamomile Extract | Soothing | 0.07 |
| B | Aloe Vera Extract (Active Organic) | Aloe Vera Extract | Healing | 0.05 |
| B | Calendula Extract | Calendula Extract | Healing | 0.05 |
| C | Preservative | QS | Antibacterial | QS |
| C | Fragrance | QS | Fragrance | QS |

Distilled water was placed in a primary tank and the remaining ingredients of Phase A were added, followed by those of Phases B and C, with mixing. pH was adjusted using 25% citric acid as required, and viscosity was adjusted with 10% NaCl solution.

Hand Lotion

The following ingredients were used to prepare the hand lotion.

TABLE 10

| Phase | Trade Name | INCI Name | Function | Amount |
|---|---|---|---|---|
| A | Distilled Water | Distilled Water | Aqua | Adjust |
| A | Glycerin | Glycerin | Humectant | 1.0 |
| A | Carbopol 940 (2% solution) | Carbomer | Thickener | 0.15 |
| B | Triple Press Stearic Acid | Stepan DGS SE | Emulsifier | 2.00 |
| B | Lipocol C | Cetyl Alcohol | Emulsifier | 1.50 |
| B | Lipo GMS-450 | Glyceryl Sterate | Emolliency | 1.50 |
| B | Shea Butter | Shea Butter | Emollient | 0.05 |
| B | Lipo IPP | Isopropyl Myristate | Emollient | 0.80 |
| B | Lipo IPM | Isopropyl Palmitate | Emollient | 0.80 |
| B | Mineral Oil | Crystosol NF 90 | Emollient | 0.50 |
| C | Skin-Flow C ™ | Wheat Starch Modified | Silky Feel | 3.00 |
| D | Japanese Green Tea Extract (Active Organic) | Green Tea Extract | Astringent | 0.05 |
| D | Goldenrod Extract (Active Organic) | Goldenrod Extract | Astringent | 0.05 |
| D | Aloe Vera (Active Organic) | Aloe Vera | Healing | 0.05 |
| D | Yucca Extract (Active Organic) | Yucca Extract | Stimulant | 0.03 |
| B | Jojoba Amino Acid | Jojoba Amino Acid | Moisturizer/ Anti-Wrinkle | 2.00 |
| E | Preservative | QS | Antibacterial | QS |

The distilled water was placed in a mixing tank along with the glycerine, and the mixture was heated to 75° C. The ingredients of Phase B were placed in a secondary tank and also heated to 75° C. Phase B was then added to Phase A at 75° C. and good agitation. The mixture was then allowed to cool to 65° C. and the ingredient of Phase C was added, making sure that there were no lumps or powder remaining on the side of the tank. The ingredients of Phase D were added in the listed order. The mixture was then cooled to 35° C. and the jojoba amino acid product 44 was added along with preservative. PH is adjusted with 99% triethanolamine as required.

Moisturizing Hand Cream

The following ingredients were used to prepare the hand cream.

TABLE 11

| Phase | Trade Name | INCI Name | Function | Amount |
|---|---|---|---|---|
| A | Distilled Water | Distilled Water | Aqua | QS |
| A | Propylene Glycol | Propylene Glycol | Humectant | 1.0 |
| A | Completech MBAC-DS | Milk Protein | Skin Feel | 0.50 |
| A | Carbomer 940 (2% solution) | Carbomer | Thickener | 0.50 |
| B | Stepan DGS SE | Triple Press Stearic Acid | Emulsifier | 3.00 |
| B | Lipocol C | Cetyl Alcohol | Emulsifier | 2.00 |
| B | Lipo GMS-450 | Glyceryl Stearate | Emulsifier | 1.75 |
| B | Shea Butter | Shea Butter | Emollient | 0.16 |
| B | Lipo IPP | Isopropyl Myristate | Emollient | 1.00 |
| B | Lipo IPM | Isopropyl Palmitate | Emollient | 1.00 |
| B | Crystosol NF 90 | Mineral Oil | Emollient | 0.50 |
| C | Skin-Flow C ™ | Wheat Starch Modified | Silky Feel | 6.64 |
| D | Japanese Green Tea Extract (Active Organic) | Green Tea Extract | Astringent | 0.05 |
| D | Goldenrod Extract (Active Organic) | Goldenrod Extract | Astringent | 0.05 |
| D | Aloe Vera (Active Organic) | Aloe Vera | Healing | 0.05 |
| D | Yucca Extract (Active Organic) | Yucca Extract | Stimulant | 0.03 |
| E | Jojoba Amino Acid | Jojoba Amino Acid | Anti-Wrinkle/ Moisturizer | 1.00 |
| E | Preservative | QS | Antibacterial | QS |

TABLE 11-continued

| Phase | Trade Name | INCI Name | Function | Amount |
|---|---|---|---|---|
| E | Jojoba Protein | Hydrolyzed Jojoba Protein | Reparative/substantivity | 1.50 |

The distilled water and other ingredients of Phase A were placed in a primary tank and heated to 75° C. The ingredients of Phase B were placed in a secondary tank and also heated to 75° C. The Phase B ingredients were added to the Phase A ingredients at 75° C. with good agitation. The mixture was then allowed to cool and at 50–55° C. the ingredient of Phase C was added, making sure that there were no lumps or powder remaining in the tank. The ingredients of Phase D were then added in the order listed. The mixture was then allowed to cool to 35° C., whereupon the jojoba amino acid product and preservative were added. pH was adjusted with 99% triethanolamine as required.

Moisturizing Foot Cream

The following ingredients were used to prepare the foot cream.

TABLE 12

| Phase | Trade Name | INCI Name | Function | Amount |
|---|---|---|---|---|
| A | Distilled Water | Distilled Water | Aqua | QS |
| A | Glycerin USP | Glycerin | Humectant | 0.5 |
| A | TEA 99% | Triethanolamine | pH adjuster | QS |
| A | Milk Protein | Milk Glyceride | Film forming | 0.50 |
| A | Cosmogel-40 | Wheat Starch | Thickener | 1.0 |
| B | Lipocol S | Stearic Acid | Emulsifier | 3.00 |
| B | Lipocol C | Cetyl Alcohol | Emulsifier | 2.00 |
| B | Lipo GMS-450 | Glyceryl Stearate | Emulsifier | 1.75 |
| B | Aqua Pro II ™ WGO | Wheat Germ Oil | Anti-Oxidant | 0.50 |
| B | Cocobutter | Cocobutter | Emollient | .20 |
| B | Lipo IPM | Isopropyl Myristate | Emollient | .50 |
| B | Lipo IPP | Isopropyl Palmitate | Emollient | .50 |
| C | Skin-Flow C ™ | Modified Wheat Starch | Skin Feel | 2.00 |
| D | Calendula Extract | Calendula Extract | Healing | 0.05 |
| D | Chamomile Extract | Chamomile Extract | Astringent | 0.05 |
| D | Aloe Vera Extract | Aloe Vera Extract | Healing | 0.05 |
| D | Jojoba Protein | Hydrolyzed Jojoba Protein | Moisturizer | 2.00 |
| D | Jojoba Amino Acid | Jojoba Amino Acid | Moisturizer | 1.00 |
| D | Menthyl Crystal | Menthyl Crystal | Cooling | 0.20 |
| D | Peppermint Oil | Peppermint Oil | Refresher | 1.00 |
| D | Preservative | Preservative | QS | QS |
| E | Yellow #5 | FD&C Yellow #5 | QS | QS |
| E | Blue #1 | FD&C Blue #1 | QS | QS |

Distilled water was metered into a primary tank, followed by mixing in Cosmogel-40 with good agitation at 40° C. When the Cosmogel-40 was in solution, the remaining Phase A ingredients were added with heating to 75° C. All of the ingredients in Phase B were weighed in another tank and heated to 75° C. Phase B was then added to Phase A with good agitation, and when the temperature reached 50–55° C., the Skin-Flow-C wheat starch product was added, making sure there were no lumps or powder remaining on the side of the tank. The Phase B ingredients were then added in the listed order, followed by color addition and pH adjustment to 5.5–6.5.

Moisturizing Foundation

The following ingredients were used to prepare the foundation.

TABLE 13

| Phase | Trade Name | INCI Name | Function | Amount |
|---|---|---|---|---|
| A | Deionized Water | Distilled Water | Aqua | QS |
| A | TEA | Triethanolamine | Humectant | 0.5 |
| A | Propylene Glycol | Propylene Glycol | Humectant | QS |
| A | Carbomer-940 | Carbomer | Viscosity | 0.20 |
| A | Veegum | Magnesium Aluminum Silicate | Viscosity | 0.30 |
| B | Steric Acid | Triple Press Stearic Acid | Emulsifier | 1.00 |
| B | Glucamate SSE-20 | PEG-20 Dimethyl Glucose Sesqusterate | Conditioning | 1.00 |
| B | Ritacol 1000 | Sterate-20 | Emulsifier | 0.80 |
| B | Lipocol C | Cetyl Alcohol | Emulsifier | 0.50 |
| B | Lipocol SC-20 | Ceteth-20 | Emulsifier | 0.50 |
| B | Glucate SS | Isopropyl Myristate | Emollient | .50 |
| B | Orgasol 2002 Ex | Nylon-12 | Biner | 3.50 |
| C | Isopar-G | C10–11 Isoparaffin | Solvent | 0.20 |
| D | Cab-O-Sil | Silica Dimethyl Siliylate | Bulking | 1.00 |
| D | Dow Corning 244 | Cyclomethicone | Feel | 15.00 |
| E | Eusolex T-200 | Titanium Dioxide | UV Protection | 2.00 |
| E | Iron Oxide Yellow | Iron Oxide Yellow | Color | 0.40 |
| E | Iron Oxide Black | Iron Oxide Black | Color | 0.40 |
| E | Iron Oxide Red | Iron Oxide Red | Color | 0.30 |
| F | Tween-20 | Polysorbate-20 | Surfactant | 1.00 |
| F | Jojoba Protein | Hydrolyzed Jojoba Protein | Anti-Wrinkle | 1.00 |
| F | Jojoba Amino Acid | Jojoba Amino Acid | Anti-Wrinkle | 2.00 |
| G | Skin Flow-C ™ | Modified Wheat Starch | Silky Feel | 2.00 |
| H | Preservative | QS | Antibacterial | QS |
| I | Fragrance | QS | Fragrance | QS |

The ingredients of Phase A were heated to 75° C., and the ingredients of Phase E were passed through a colloid mill with some propylene glycol and recirculation until the pigments were evenly dispersed. The colloid mill was rinsed with the Phase C ingredient and mixed using a lightnin mixer with heating to 75° C. Phase B components were premixed and heated to 75° C., and added to the main batch. The Phase G ingredient was then sprinkled into the main batch premix Phase D with heating to 65° C. At 40° C., the ingredients of Phase F were added to the main batch together with preservative and fragrance.

Moisturizing Baby Cream

The following ingredients were used to prepare the baby cream.

TABLE 14

| Phase | Trade Name | INCI Name | Function | Amount |
|---|---|---|---|---|
| A | Distilled Water | Distilled Water | Aqua | QS |
| A | Glycerin | Glycerin USP | Humectant | 2.50 |
| B | Lipocol S | Stearic Acid | Emulsifier | 3.00 |
| B | Lipocol C | Cetyl Alcohol | Emulsifier | 3.50 |
| B | Lipowax G | Stearyl Alcohol | Emulsifier | 2.00 |
| B | Lipo GMS-450 | Glyceryl Sterate | Emulsifier | 2.50 |
| B | Dow Corning 200 Fluid | Dimethicone | Film Former | 1.00 |
| B | Aqua Pro ™II WGO | Wheat Germ Oil | Anti-Oxidant | 0.50 |
| C | Skin-Flow-C ™ | Modified Wheat Starch | Silky Feel/Thickener | 6.50 |
| D | Jojoba Protein | Hydrolyzed Jooba Protein | Moisturizer/Anti-Wrinkle | 1.00 |

TABLE 14-continued

| Phase | Trade Name | INCI Name | Function | Amount |
|---|---|---|---|---|
| F | Jojoba Amino Acid | Jojoba Amino Acid | Moisturizer/Anti-Wrinkle | 2.00 |
| H | Preservative | QS | Antibacterial | QS |

Distilled water was metered into a primary tank and the glycerine was added with heating to 75° C. The Phase B ingredients were added in order to a secondary tank and heated to 75° C. The Phase B ingredients were added to the Phase A ingredients with good agitation. When the temperature reached 50–55° C., the Skin-Flow-C product was shifted into the batch, making sure there were no lumps or powder. The Phase D ingredients were added, and at 35° C., the preservative was added with pH adjustment to 3.5–4.5.

Anti-Wrinkle Cream

The following ingredients were used to prepare the anti-wrinkle cream.

TABLE 15

| Phase | Trade Name | INCI Name | Function | Amount |
|---|---|---|---|---|
| A | Distilled Water | Distilled Water | Aqua | QS |
| A | Glycerin | Glycerin USP | Humectant | 1.0 |
| A | Milk Protein | Completech MBAC-DS | Skin Feel | 0.50 |
| A | Carbomer 940 (2% solution) | Carbomer | Thickener | 0.50 |
| B | Stepan DGS SE | Triple Press Stearic Acid | Emulsifier | 3.00 |
| B | Lipocol C | Cetyl Alcohol | Emulsifier | 2.00 |
| B | Lipo GMS-450 | Glyceryl Stearate | Emulsifier | 1.75 |
| B | Promulgin D | Cetearyl Alcohol Ceteareth-20 | Emulsifier | 1.00 |
| B | Coco Butter | Coco Butter | Emollient | 0.50 |
| B | Lipo IPP | Isopropyl Myristate | Emollient | 1.50 |
| B | Lipo IPM | Isopropyl Palmitate | Emollient | 1.50 |
| B | Crystisik NF 90 | Mineral Oil | Emollient | 0.50 |
| C | Skin-Flow-C ® | Wheat Starch Modified | Silky Feel | 3.00 |
| F | Jojoba Protein | Hydrolyzed Jojoba Protein | Anti-Wrinkle | 0.50 |
| F | Jojoba Amino Acid | Jojoba Amino Acid | Anti-Wrinkle | 2.00 |
| H | Preservative | QS | Antibacterial | QS |

The distilled water was added to a primary tank followed by the ingredients of Phase A, with heating to 75° C. The Phase B ingredients were added in order to a secondary tank and heated to 75° C. Phase B was added to Phase A at 75° C. with good agitation. At 50–55° C., the Skin-Flow-C product was added, making sure there were no lumps or powder remaining. When the temperature reached 35° C., the jojoba amino acid and hydrolyzed jojoba protein were added, together with the preservative.

Hair Styling Gel

The following ingredients were used to prepare the hair styling gel.

TABLE 16

| Phase | Trade Name | INCI Name | Function | Amount |
|---|---|---|---|---|
| A | Deionized Water | Deionized Water | Aqua | QS |
| A | Luviskol K30 | PVPethanolamine | Fixative | 1.80 |
| A | TEA (25%) | Triethanolamine | pH Adjuster | QS |
| A | Carbomer-940 | Carbopol | Thickener | 1.00 |

TABLE 16-continued

| Phase | Trade Name | INCI Name | Function | Amount |
|---|---|---|---|---|
| A | Glucame-E20 | Methyl Gluceth-20 | Film Former | 0.50 |
| A | Versene NA2 | Disodium EDTA | Chelation | 0.50 |
| B | Tween-20 | Polysorbate-20 | Cleansing | 1.50 |
| B | Uvasorb S5 | Benzophenone-4 | UV Protection | 0.04 |
| B | Jojoba Protein | Hydrolyzed Jojoba Protein | Reparative | 3.00 |
| C | Preservative | QS | Antibacterial | QS |
| C | Fragrance | QS | Fragrance | QS |

The Carbomer was added in 25% water followed by mixing in of Phase A ingredients in order. Next, the Phase B ingredients were added with good agitation, followed by addition of preservative and fragrance. The pH of the product was 5.5.

Face Mask

The following ingredients were used to prepare the face mask.

TABLE 17

| Phase | Trade Name | INCI Name | Function | Amount |
|---|---|---|---|---|
| A | Deionized Water | Distilled Water | Aqua | Adjust |
| A | Propylene Glycol | Propylene Glycol | Humectant | 1.50 |
| B | Lipocol GMS-450 | Glyceryl Sterate | Emulsifier | 2.00 |
| B | Lipowax G | Stearyl Alcohol | Emulsifier | 2.50 |
| B | Lipocol C | Cetyl Alcohol | Emulsifier | 2.00 |
| C | Skin-Flow-C ™ | Wheat Starch Modified | Skin Feel | 2.00 |
| D | Kaoline | Kaoline Colloidal NF | Firming | 10.00 |
| D | Bentonite | Bentonite 670 | Firming | 8.00 |
| E | Aqua Pro II ™ CO | Colloidal Oat | Anti-Wrinkle | 5.00 |
| E | Jojoba Protein | Hydrolyzed Jojoba Protein | Anti-Wrinkle | 1.00 |
| E | Jojoba Amino Acid | Jojoba Amino Acid | Anti-Wrinkle | 2.00 |
| F | Preservative | QS | Antibacterial | QS |

The Phase A and Phase B ingredients were separately heated to 75° C., and Phase B was added to Phase A with mixing. When the mixture reached 65° C., the Phase C ingredient was added with good mixing. Thereafter, the Phase D ingredients were added and the mixture was cooled to 35° C., whereupon the Phase E ingredients were added along with the preservative.

We claim:

1. An unhydrolyzed jojoba protein composition comprising from about 11–18% by weight simmondsin, and from about 10–30% by weight unhydrolyzed protein, said unhydrolyzed jojoba protein composition having an average protein molecular weight that is 200–880,000 daltons.

2. The composition of claim 1, said unhydrolyzed protein derivatized by treatment with 3-chloro-2-hydroxypropyl-N,N,N-dimethyldodecylammonium chloride.

3. An aqueous dispersion containing unhydrolyzed jojoba protein including a solid phase comprising from about 11–18% by weight simmondsin, and from about 10–30% by weight unhydrolyzed protein, said unhydrolyzed jojoba protein composition having an average protein molecular weight that is 200–880,000 daltons 4,000.

* * * * *